US00PP18874P2

(12) United States Plant Patent
Meilland

(10) Patent No.: US PP18,874 P2
(45) Date of Patent: Jun. 3, 2008

(54) SHRUB ROSE PLANT NAMED 'MEIJOCOS'

(50) Latin Name: *Rosa hybrida*
Varietal Denomination: Meijocos

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 72 days.

(21) Appl. No.: 11/523,037

(22) Filed: Sep. 19, 2006

(51) Int. Cl.
*A01H 5/00* (2006.01)

(52) U.S. Cl. ..... Plt./102

(58) Field of Classification Search ..... Plt./102
See application file for complete search history.

*Primary Examiner*—Annette H Para
(74) *Attorney, Agent, or Firm*—Buchanan Ingersoll & Rooney PC

(57) ABSTRACT

A new and distinct variety of shrub rose plant is provided which forms in abundance in clusters on a nearly continuous basis attractive semi-double fragrant deep pink blossoms that clean well having a light eye. A spreading ground cover growth habit with procumbent vegetation is displayed. Attractive glossy dark green foliage is formed. The plant develops well following asexual reproduction, and is highly resistant to Black Spot, Powdery Mildew, and Rust. The new variety is particularly well suited for growing as ornamentation in the landscape as a mass planting or for growing in containers.

3 Drawing Sheets

Botanical/commercial classification: *Rosa hybrida*/Shrub Rose Plant.
Varietal denomination: cv. Meijocos.

SUMMARY OF THE INVENTION

The new variety of *Rosa hybrida* shrub rose plant of the present invention was created by artificial pollination wherein two parents were crossed which previously had been studied in the hope that they would contribute the desired characteristics. The female parent (i.e., the seed parent) was the 'Korimro' variety (non-patented in the United States). The male parent (i.e., the pollen parent) of the new variety was an unnamed and unreleased seedling (non-patented in the United States). The parentage of the new variety can be summarized as follows:

*'Korimro'×Unnamed Seedling.*

The seeds resulting from the above pollination were sown and small plants were obtained which were physically and biologically different from each other. Selective study resulted in the identification of a single plant of the new variety.

It was found that the new shrub rose plant of the present invention possesses the following combination of characteristics:

(a) abundantly forms in clusters on a nearly continuous basis attractive semi-double fragrant deep pink blossoms that clean well having a light eye, (b) exhibits a spreading ground cover growth habit with procumbent vegetation, (c) forms attractive dark green foliage with a glossy finish that contrasts well with the blossom coloration, (d) develops well following asexual reproduction, (e) is highly resistant to Black Spot, Powdery Mildew, and Rust, and (f) is particularly well suited for providing attractive ornamentation in the landscape as a mass planting or when grown in containers.

Good plant development is displayed regardless of the mode of asexual propagation.

The new variety well meets the needs of the horticultural industry. It can be grown to advantage as ornamentation in parks, gardens, public areas, and in residential settings. The new variety is particularly well suited for growing in smaller areas as a ground cover and as a mass planting in a larger area.

The new variety of the present invention also can be readily distinguished from its ancestors. More specifically, the 'Korimro' variety forms single light pink flowers unlike the semi-double deep pink flowers of the new variety having a light eye.

Additionally, the new variety can be readily distinguished from other similar rose varieties, such as the 'Meilmera' variety (U.S. Plant Pat. No. 10,002) and the 'Meidarin' variety (U.S. Plant Pat. No. 13,291). The 'Meilmera' variety has a similar growth habit, but displays white blossoms and is considerably less hardy. The 'Meidarin' variety also displays a similar growth habit, but displays vibrant orange blossoms and also is considerably less hardy.

The characteristics of the new variety have been found at Waso, Calif. U.S.A., and near West Grove, Pa., U.S.A., to be homogeneous and stable and to be strictly transmissible by asexual propagation such as budding, grafting, and the rooting of cuttings from one generation to another. The new variety reproduces true to type by such asexual propagation.

The new variety has been named 'Meijocos', and is being marketed under the PINK DRIFT trademark.

BRIEF DESCRIPTION OF THE PHOTOGRAPHS

The accompanying photographs show, as nearly true as it is reasonably possible to make the same in color illustrations of this character, typical flowering plants of the new variety. The illustrated rose plants of the new variety were approximately three years of age and were observed during June while growing outdoors on 'Dr. Huey' rootstock near West Grove, Pa., U.S.A.

DETAILED DESCRIPTION

Figure 1:
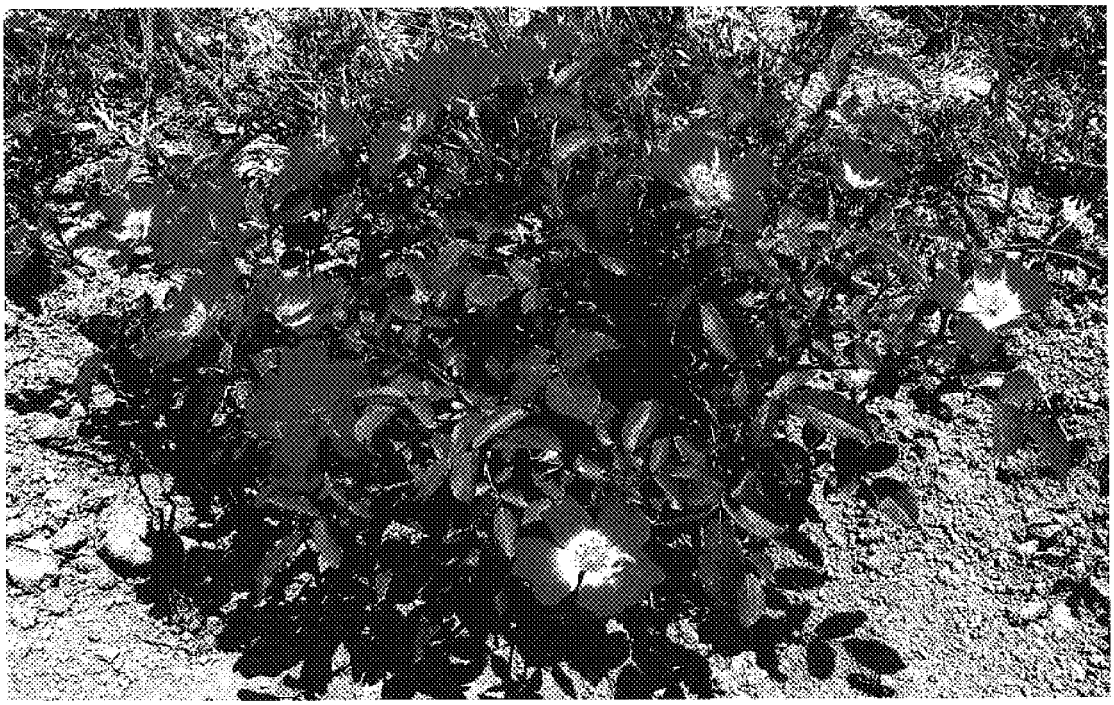
FIG. 1 shows from above a specimen of a single flowering plant of the new variety.
Figure 2:
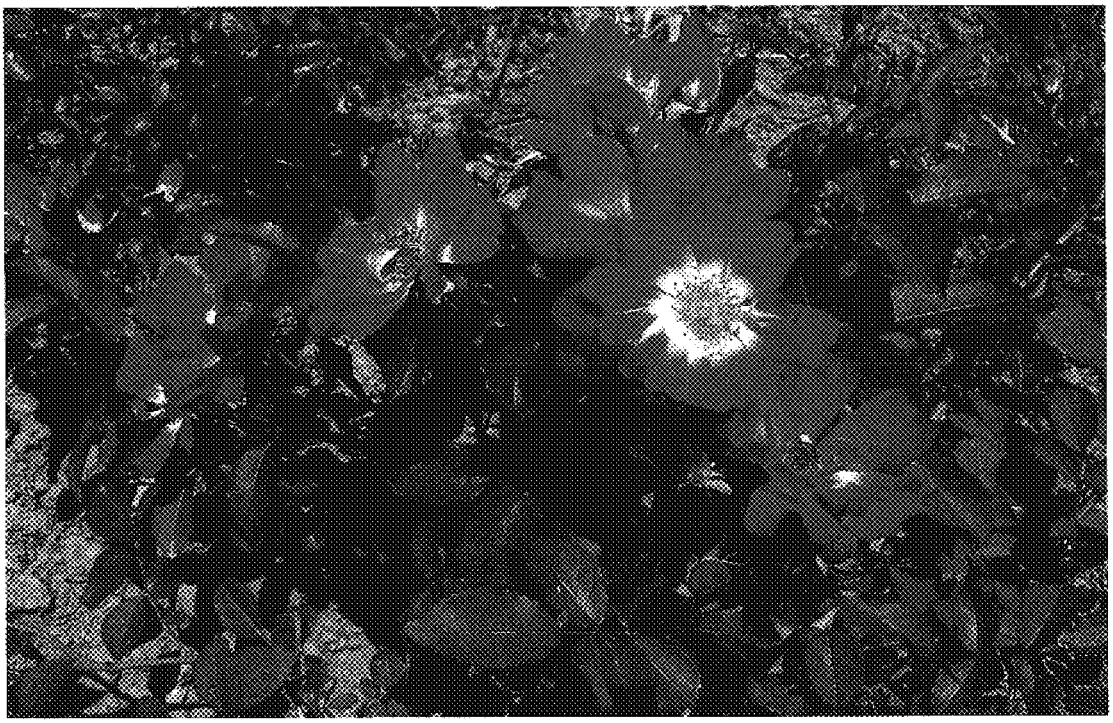
FIG. 2 shows a closer view of the buds, blossoms, and attractive glossy dark green foliage of the new variety.
Figure 3:
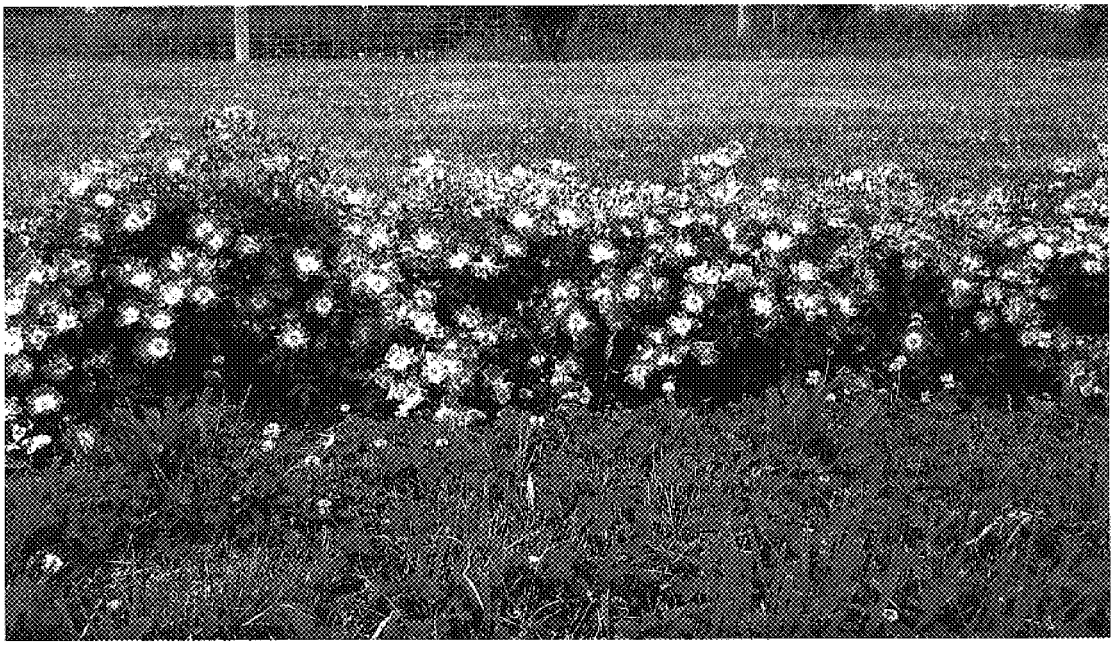
FIG. 3 shows a mass planting of the new variety wherein the procumbent character of branching is illustrated.

The chart used in the identification of colors is that of The Royal Horticultural Society (R.H.S. Colour Chart), London, England. The description is based on the observation of three-year-old specimens of the new variety during June while growing outdoors on 'Dr. Huey' rootstock near West Grove, Pa., U.S.A.

Class: Landscape Shrub.

Plant:

*Height.*—Approximately 30 to 45 cm on average at the end of the growing season.

*Width.*—Approximately 75 to 90 cm on average at the end of the growing season.

*Habit.*—As a low rounded mound.

Branches:

*Thorns.*—Size: relatively small, and approximately 1 cm in length. Configuration: commonly sharply pointed with the terminal portion nearly perpendicular to the stem and pointing upward. Quantity: commonly approximately 4 or 5 over a stem length of 10 cm. Color: on young stems near Yellow-Green Group 151A, and on mature wood Brown Group 200D and more glabrous.

Leaves:

*Length.*—Approximately 8 to 9 cm in length including the petiole for a five-leaflet leaf, and approximately 11 to 12 cm in length including the petiole for a seven-leaflet leaf.

*Width.*—Approximately 6 to 6.5 cm at the widest point for a five-leaflet leaf, and approximately 6 to 6.5 cm at the widest point for a seven-leaflet leaf.

*Leaflets.*—Number. 3, 5, 7, and rarely 9. Arrangement: alternate and pinnate. Shape: typically elliptical to broadly elliptical with a broadly acute to rounded apex, and a shortly attenuate base. Margins: serrulate. Texture: glabrous on both surfaces and papyraceus. Overall appearance: dense, small, dark green, and glossy. Color (young foliage): upper surface: near Yellow-Green Group 144A with some coloration of Red Group 46A at the edges. Under surface: near Yellow-Green Group 144D. Color (adult foliage): upper surface: near Green Group 137A. Under surface: near Green Group 138B with some lightening to Green Group 137C.

Inflorescence:

*Number of flowers.*—Commonly approximately 8 to 12 blooms on average in a cluster.

*Peduncle.*—Approximately 30 to 35 mm in length on average, and approximately 1 to 1.5 mm in diameter on average.

*Sepals.*—Typically five and sometimes six in number, lanceolate in configuration, approximately 15 to 18 mm in length on average, approximately 4 mm in width on average, near Green Group 137C on the outer surface, near Yellow-Green Group 143B on the inner surfaces, and with a sparse number of foliaceous extensions.

*Buds.*—Shape: ovoid. Size: very small. Length: approximately 1.5 cm on average as the calyx breaks. Width: approximately 0.6 mm on average as the calyx breaks. Color (upper surface): as the buds crack, Red Group 45A at the apex and Yellow Group 15C at the base. Color (under surface): as the buds crack, Red Group 53C at the apex and Yellow Group 15D at the base.

Flower. —Form: semi-double. Shape: flat when fully open. Diameter: approximately 4.5 to 5 cm. on average when fully open. Color (when newly open): upper surface: Red-Purple Group 58B at the apex and Yellow Group 7D at the base. Under surface: Red-Purple Group 58B at the apex and Yellow Group 7D at the base. Color (when fully open): upper surface: Red-Purple Group 57B at the apex with a small amount of Yellow Group 8D at the base. Under surface: Red-Purple Group 57D at the apex and White Group 155B at the base. Color stability: no significant color change as the blooms reach full maturity. Fragrance: medium intensity. Petal shape: obovate to narrowly obovate to narrowly obcordate. Petal number: commonly approximately 8 to 11 on average under normal growing conditions. Petal texture: glabrous, membranaceus, relatively thin, and semi-transparent. Petal margin: entire, but tends to be revolute to a slight degree. Petal apex: obtuse. Petal base: narrowly cuneatus. Petal size: commonly approximately 2 to 2.5 cm in length, and approximately 1.5 to 1.8 cm in width. Petal drop: very good with the petals detaching cleanly before drying. Petaloids: typically approximately 1 to 3 per blossom, irregularly shaped, approximately 14 mm in length on average, and approximately 8 mm in width on average. Stamen number: approximately 95 to 100 on average. Filaments: typically approximately 6 mm in length and less than 1 mm in diameter. Pollen: near Yellow-Orange Group 22A in coloration. Pistils: typically approximately 12 in number. Styles: approximately 5 mm in length, and less than 1 mm in diameter. Receptacle: slightly glaucous, approximately 5 to 6 mm in size when the flower is fully open, and near Green Group 138A in coloration. Hips: rarely observed.

Development:

*Vegetation.*—Vigous procumbent thin branches with thin upright shoots and as generally restrained growth habit.

*Blossoming.*—Abundant and nearly continuous.

*Resistance to diseases.*—Excellent with respect to Black Spot, Powdery Mildew, and Rust when compared to other commercial varieties under comparable growing conditions near West Grove, Pa., U.S.A.

*Formation of hips/seeds.*—Very sparse.

I claim:

1. A new and distinct shrub rose plant characterized by the following combination of characteristics:

(a) abundantly forms in clusters on a nearly continuous basis attractive semi-double fragrant deep pink blossoms that clean well having a light eye, (b) exhibits a spreading ground cover growth habit with procumbent vegetation, (c) forms attractive dark green foliage with a glossy finish that contrasts well with the blossom coloration, (d) develops well following asexual reproduction, (e) is highly resistant to Black Spot, Powdery Mildew, and Rust, and (f) is particularly well suited for providing attractive ornamentation in the landscape as a mass planting or when grown in containers;

substantially as herein shown and described.

* * * * *